United States Patent [19]

Kohno et al.

[11] Patent Number: 4,966,899

[45] Date of Patent: Oct. 30, 1990

[54] ANTIBACTERIAL LYOPHILIZED PREPARATION OF ASPOXICILLIN

[75] Inventors: Keiichi Kohno, Toyonaka; Hiroshi Miura, Takatsuki; Yoshiyuki Hirakawa; Toshiyuki Ueki, both of Toyonaka; Seiichi Morikuni, Onoda, all of Japan

[73] Assignee: Tanabe Seiyaku Co., Ltd., Osaka, Japan

[21] Appl. No.: 143,769

[22] Filed: Jan. 14, 1988

[30] Foreign Application Priority Data

Jan. 14, 1987 [JP]  Japan .................................. 62-06868

[51] Int. Cl.$^5$ .............................................. A61K 31/43
[52] U.S. Cl. .................................... 514/197; 540/332
[58] Field of Search ................. 514/197; 540/332, 322

[56] References Cited

U.S. PATENT DOCUMENTS

| | | | |
|---|---|---|---|
| 3,733,404 | 5/1973 | Cyr et al. | 424/114 |
| 4,053,609 | 10/1977 | Kawazu et al. | 260/239.1 |
| 4,130,558 | 12/1978 | Ross et al. | 540/323 |
| 4,313,875 | 2/1982 | Nakamura et al. | 514/197 |

FOREIGN PATENT DOCUMENTS 1539510 1/1979 United Kingdom .

OTHER PUBLICATIONS

The Journal of Antibiotics, vol. 36, No. 2, Feb. 1983, pp. 147–154; Mitsuyoshi Wagatsuma et al.
Chemical Abstracts of Japan, vol. 90, No. 26, Jun. 25th, 1979, p. 398, Abstract No. 210120y.

*Primary Examiner*—Douglas W. Robinson
*Assistant Examiner*—Zohreh A. Fay
*Attorney, Agent, or Firm*—Birch, Stewart, Kolasch & Birch

[57]  ABSTRACT

An antibacterial lyophilized preparation which comprises as an active ingredient aspoxicillin and a basic salt of aspoxicillin in a molar ratio of 1 : about 0.7 to 7 and optionally an alkali metal halide as a stabilizer, and a method for preparing the same, said antibacterial lyophilized preparation being able to be rapidly dissolved in distilled water to give a stable solution which can be injected to patients for the treatment of various bacterial infectious diseases.

7 Claims, No Drawings

ANTIBACTERIAL LYOPHILIZED PREPARATION OF ASPOXICILLIN

This invention relates to a novel antibacterial lyophilized preparation, more particularly to an antibacterial lyophilized preparation containing as an active ingredient aspoxicillin.

PRIOR ART

It is known that aspoxicillin (chemical name: (2S, 5R, 6R)-6-[(2R)-2-[(2R)-2-amino-3-(N-methylcarbamoyl)-propionamido]-2-(p-hydroxyphenyl)acetamido]-3,3-dimethyl-7-oxo-4-thia-1-azabicyclo[3.2.0]heptane-2-carboxylic acid) has potent antibacterial activities against gram positive bacteria and gram negative bacteria and hence is useful as an excellent antibacterial agent (cf. Japanese Patent Second Publication (Kokoku) No. 43519/1979), and further that when an aqueous solution containing crude aspoxicillin is treated with a nonpolar porous adsorbent resin to purify and then lyophilized, there can be obtained a highly pure, powdery aspoxicillin (cf. Japanese Patent First Publication (Kokai) No. 40686/1981).

However, the aspoxicillin obtained by the method as disclosed in the above Japanese Patent first Publication No. 40686/1981 is an amorphous anhydride product and is hygroscopic, and hence, it is not enough stable unless it is kept under moisture-proof and light protecting conditions.

It has been found that when the above aspoxicillin is crystallized from an aqueous solution thereof under a weak acidic condition, it can be obtained in the form of a novel crystalline trihydrate which has excellent characteristics as a medical substance, such as small bulk density and less static electrification (cf. Japanese Patent Application No. 226423/1986), but the aspoxicillin trihydrate thus obtained has less water-solubility (i.e., 2.8 g/100 ml of water at 0° C.), and hence, it can hardly be used for preparing an injection. Generally, antibacterial injections are preferred to be kept in the form of a solid in view of storage stability and be reconstituted with a suitable solvent (e.g. purified water for injection) when used. However, the above aspoxicillin trihydrate has less water-solubility, and hence, in order to use the substance in the form of a solid preparation, it must be dissolved in a too large a volume of a solvent to administered to a patient. The resultant injection thus obtained is impractical to administer either in a single shot or in a combined infusion with other injections, because it requires too long period of time for administration and hence gives much load to the patient.

On the other hand, it is known that in order to dissolve such hardly soluble substances in water, the substances are modified so as to have a large surface area, for example by making them amorphous by an appropriate means, such as lyophilization. However, for applying this method to the aspoxicillin trihydrate, it must be dissolved in water which is a solvent for the lyophilization, and hence, a large amount of the solvent is required. Moreover, the large amount of solvent must be removed by the lyophilization, which requires a large scale of an apparatus.

BRIEF DESCRIPTION OF THE INVENTION

The present inventors have intentively studied to prepare a lyophilization preparation of aspoxicillin without the troublesome treatment and without a specific apparatus, and have now found that when a part of aspoxicillin is used in the form of a basic salt thereof, the mixture of free aspoxicillin and a basic salt of aspoxicillin can easily be lyophilized to give the desired lyophilized preparation.

An object of the invention is to provide a novel antibacterial lyophilized preparation containing as an active ingredient aspoxicillin. Another object of the invention is to provide an antibacterial lyophilized preparation of aspoxicillin which is easily dissolved in distilled water for injection and hence is suitable as an injection for the treatment of various bacterial infectious diseases. These and other objects and advantages of the invention will be apparent to those skilled in the art from the following description.

DETAILED DESCRIPTION OF THE INVENTION

The antibacterial lyophilized preparation of this invention comprises aspoxicillin and a basic salt of aspoxicillin in a molar ratio of 1 : about 0.7 to 7.

Thus the preparation of this invention comprises a specific ratio of aspoxicillin and a basic salt of aspoxicillin (hereinafter, referred merely to as "aspoxicillin salt") and can be prepared by using not only amorphous anhydride of aspoxicillin but also aspoxicillin trihydrate which has hitherto hardly been used for injection preparation because of less water solubility as mentioned hereinbefore. Furthermore, the preparation of this invention has advantages in that it can easily be dissolved in distilled water for injection, and further that there can be obtained an injection preparation containing a high concentration of aspoxicillin.

The aspoxicillin salt used in this invention includes, for example, aspoxicillin alkali metal salts (e.g. potassium salt, sodium salt, etc.), basic amino acid salts (e.g. lysine salt, arginine salt, ornithine salt, etc.), trishydroxymethylaminomethane salt, and the like.

In the preparation of this invention, the aspoxicillin and aspoxicillin salt are mixed in a specific molar ratio, that is, about 0.7 to 7 mole, preferably about 1.5 to 7 mole, more preferably about 2 to 6 mole, of aspoxicillin salt to 1 mole of aspoxicillin.

The preparation of this invention may optionally be incorporated with an alkali metal halide, such as sodium chloride, potassium chloride, as a stabilizer. Particularly preferred stabilizer is sodium chloride. The alkali metal halide is preferably incorporated in an amount of about 0.2 to 0.7 mole, more preferably about 0.4 to 0.7 mole, to 1 mole of whole of aspoxicillin and aspoxicillin salt.

The preparation of this invention may also optionally be incorporated with conventional additives, such as isotonic agents, anesthetizing agents, buffering agents, and the like.

The preparation of this invention can be prepared by a conventional method for preparing conventional lyophilization preparation for injection.

That is, aspoxicillin, aspoxicillin salt, and optionally an alkali metal halide as a stabilizer and further optionally other additives are dissolved in distilled water for injection, and the solution is lyophilized to give the desired preparation. In this preparation method, there may be used aspoxicillin and a pharmaceutically acceptable basic substance instead of aspoxicillin salt, and thereby, the aspoxicillin salt is formed when they are dissolved in the distilled water.

The aspoxicillin used in this invention may be in the form of an amorphous anhydride or a crystalline trihydrate. The basic substance includes, for example, alkali metal hydroxides (e.g. potassium hydroxide, sodium hydroxide, etc.), alkali metal carbonates (e.g. potassium carbonate, sodium carbonate, etc.), alkali metal hydrogen carbonates (e.g. potassium hydrogen carbonate, sodium hydrogen carbonate, etc.), basic amino acids (e.g. lysine, arginine, ornithine, etc.), trishydroxymethylaminomethane, and the like. Particularly preferred basic substances are sodium hydroxide, potassium hydroxide, and sodium carbonate.

When aspoxicillin and aspoxicillin salt are used for preparing the desired preparation, these are used in a ratio of about 0.7 to 7 mole of aspoxicillin to 1 mole of aspoxicillin. In case of preparing the preparation by using aspoxicillin and a basic substance, the basic substance is used in an amount of about 0.4 to 0.88 mole to 1 mole of aspoxicillin, by which the aspoxicillin salt is formed in an amount of about 0.7 to 7 mole to 1 mole of aspoxicillin when they are dissolved in the distilled water for injection. Besides, within the above amount, there can be prepared the desired preparation containing a high concentration of aspoxicillin. The aspoxicillin salt or the basic substance may be used in excess amount than the above-mentioned molar ratios, and in this case, the solution prepared by dissolving these substances in distilled water for injection is adjusted to pH 7 to 7.5 with an acid such as hydrochloric acid, acetic acid, succinic acid, citric acid, and the like.

The solution thus prepared can easily be lyophilized by a conventional method, for example, by filling the solution in an ampoule or a vial and then rapidly freezing by cooling at $-30°$ C. to $-40°$ C., and removing moisture for 5 to 70 hours under 0.05 to 0.5 torr, while supplementing heat necessary for removal of moisture.

The antibacterial lyophilized preparation of this invention thus obtained has excellent storage stability and further advantages that when it is dissolved in distilled water when used, it can rapidly be dissolved without precipitation of hardly soluble crystal to give the desired stable solution having the desired concentration of the active aspoxicillin.

The aspoxicillin trihydrate used in this invention can be prepared, for example, by dissolving aspoxicillin or a salt thereof in an aqueous solvent (e.g. water, hydrous lower alcohols, hydrous lower alkanones, etc.) and crystallizing out from the solution under a weak acidic condition (e.g. pH 3-6).

The present invention is illustrated by the following Examples but should not be construed to be limited thereto.

EXAMPLE 1

Aspoxicillin trihydrate (1.11 g) (=1 g when converted into aspoxicillin) and potassium hydroxide (0.09 g) are dissolved in distilled water for injection (5 ml), and the solution is filled in a 25 ml vial. The vial is rapidly cooled to $-35°$ C. and freezed at said temperature for 3 hours. The resultant is dried at 20 °-25° C., 0.1-0.2 torr for 30 hours, and further dried at 40°-50° C., 0.1-0.2 torr for 5 hours to give the desired antibacterial lyophilized preparation of this invention.

The antibacterial lyophilized preparation thus obtained contains aspoxicillin and aspoxicillin potassium salt in a molar ratio of 1:4. When distilled water for injection (5 ml) is added to the vial, the content of the vial is rapidly dissolved to give a clear injection solution (about pH 7.5) which contains 20 w/v % of aspoxicillin.

EXAMPLES 2 TO 4

In the same manner as described in Example 1 except that basic substances are used instead of potassium hydroxide in each amount as shown in Table 1, there are prepared antibacterial lyophilized preparations.

These antibacterial lyophilized preparations contain aspoxicillin salt in such a molar amount as shown in Table 1 per 1 mole of aspoxicillin. When distilled water for injection (5 ml) is added to the antibacterial lyophilized preparations, the content of the vials are rapidly dissolved to give clear injection solutions which contain 20 w/v % of aspoxicillin.

TABLE 1

| Ex. No. | Basic substance and amount thereof (g) | Aspoxicillin salt in the preparation (molar ratio*) |
|---|---|---|
| 2 | Sodium hydroxide (0.066) | Aspoxicillin sodium salt (4) |
| 3 | Trishydroxymethyl-aminomethane (0.020) | Aspoxicillin trishydroxymethylaminomethane salt (4) |
| 4 | Arginine (0.028) | Aspoxicillin arginine salt (4) |

*Molar number of aspoxicillin salt per 1 mole of aspoxicillin in the preparations (hereinafter the same)

EXAMPLE 5

Aspoxicillin trihydrate (1.11 g) (=1 g when converted into aspoxicillin), sodium hydroxide (0.066 g) and sodium chloride (0.05 g) are dissolved in distilled water for injection (5 ml), and the solution is treated in the same manner as described in Example 1 to give the desired antibacterial lyophilized preparation.

The antibacterial lyophilized preparation thus obtained contains aspoxicillin and aspoxicillin sodium salt in a molar ratio of 1:4 and also contains sodium chloride in an amount of 0.4 mole per 1 mole of both of the above. When distilled water for injection (5 ml) is added to the vial, the content of the vial is rapidly dissolved to give a clear injection solution (about pH 7.5) which contains 20 w/v % of aspoxicillin.

EXAMPLES 6 TO 9

In the same manner as described in Example 1 except that aspoxicillin trihydrate and sodium hydroxide are used in each amount as shown in Table 2, there are prepared antibacterial lyophilized preparations.

These antibacterial lyophilized preparations contain aspoxicillin and aspoxicillin sodium salt in such molar ratios as shown in said Table. When distilled water for injection (5 ml) is added to the preparations, the content of the vials are rapidly dissolved to give clear injection solutions which contain aspoxicillin in an amount as shown in said Table.

TABLE 2

| Ex. No. | Amount of component (g) ASPC. · 3H$_2$O | NaOH | Molar ratio | ASPC. content (w/v %) | pH |
|---|---|---|---|---|---|
| 6 | 0.420 | 0.0185 | 1.5 | 7.6 | Ca. 6.9 |
| 7 | 0.660 | 0.036 | 3 | 11.9 | Ca. 7.2 |
| 8 | 1.295 | 0.0795 | 5.3 | 23.3 | Ca. 7.5 |
| 9 | 1.955 | 0.125 | 7 | 35.2 | Ca. 7.6 |

ASPC: Aspoxicillin

REFERENCE EXAMPLE

Water (50 ml) is added to amorphous anhydride of aspoxicillin (10 g) and the mixture is heated at 40° C. for dissolving it and then adjusted to pH 4.0 with diluted hydrochloric acid. The mixture is stirred at 30° C. for one hour and then cooled to 5° C. The resulting precipitate is separated by filtration, washed with water and dried to give white aspoxicillin trihydrate (8 g).

Water content (KF): 10.05% (corresp. to 3 moles)
Aspoxicillin content (HPLC): 99.7%
Optical rotation $]\alpha]_D^{20}$: +179.5° (c=1.0, water)
X-ray diffraction pattern of the powder:
Power source (Cu:Ni, 40 KV, 35 mA, $\lambda$=1.5405)

| Distance (Å) | Relative strength (I)* |
|---|---|
| 15.77 | w |
| 10.77 | w |
| 9.21 | v w |
| 7.89 | w |
| 5.98 | s |
| 5.57 | v s |
| 5.34 | w |
| 4.98 | v w |
| 4.62 | v s |
| 4.39 | w |
| 4.23 | m |
| 3.97 | m |
| 3.77 | v w |
| 3.64 | v w |
| 3.54 | w |
| 3.48 | w |
| 3.37 | w |
| 3.25 | m |
| 3.13 | v w |
| 3.01 | w |
| 2.86 | v w |
| 2.81 | v w |
| 2.65 | v w |
| 2.60 | v w |
| 2.40 | w |

*The relative strength (I) shows the following criteria: v s: very strong, s: strong, m: medium w: weak, v w: very weak

What is claimed is:

1. A method for preparing an antibacterial lyophilized preparation containing as an active ingredient an aspoxicillin selected from aspoxicillin anhydride and aspoxicillin trihydrate, which comprises: dissolving said aspoxicillin and an alkali metal salt of aspoxicillin in a molar ratio of 1:0.7–7 and optionally an alkali metal halide in distilled water for injection; and lyophilizing the solution.

2. The method according to claim 1, wherein the alkali metal halide is sodium chloride.

3. An antibacterial lyophilized preparation which comprises an aspoxicillin selected from aspoxicillin anhydride and aspoxicillin trihydrate, and an alkali metal salt of aspoxicillin in a molar ratio of 1:about 0.7 to 7.

4. The preparation according to claim 3, wherein the molar ratio of the alkali metal salt of aspoxicillin to aspoxicillin is in the range of 1:1.5 to 1:7.

5. The preparation according to claim 3, wherein the molar ratio of the alkali metal salt of aspoxicillin to aspoxicillin is in the range of 1:2 to 1:6.

6. The preparation according to claim 5, wherein the alkali metal salt of aspoxicillin is aspoxicillin sodium salt.

7. The preparation according to claim 5, which further comprises sodium chloride in an amount of about 0.2 to 0.7 mole per mole of combined total of aspoxicillin and aspoxicillin sodium salt.

* * * * *